US011166900B2

United States Patent
Guarilloff

(10) Patent No.: US 11,166,900 B2
(45) Date of Patent: *Nov. 9, 2021

(54) POWDERY COSMETIC COMPOSITION COMPRISING NANOCRYSTALLINE CELLULOSE

(71) Applicant: Anomera Inc., Montreal (CA)

(72) Inventor: Philippe Guarilloff, Princeton, NJ (US)

(73) Assignee: Anomera Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/464,816

(22) PCT Filed: Nov. 30, 2017

(86) PCT No.: PCT/EP2017/080981
§ 371 (c)(1),
(2) Date: May 29, 2019

(87) PCT Pub. No.: WO2018/100061
PCT Pub. Date: Jun. 7, 2018

(65) Prior Publication Data
US 2019/0321278 A1    Oct. 24, 2019

Related U.S. Application Data

(60) Provisional application No. 62/427,922, filed on Nov. 30, 2016.

(51) Int. Cl.
| | | |
|---|---|---|
| *A61K 8/73* | (2006.01) | |
| *A61K 8/92* | (2006.01) | |
| *A61Q 1/02* | (2006.01) | |
| *A61Q 1/12* | (2006.01) | |
| *A61Q 17/04* | (2006.01) | |

(52) U.S. Cl.
CPC .............. *A61K 8/731* (2013.01); *A61K 8/92* (2013.01); *A61Q 1/02* (2013.01); *A61Q 1/12* (2013.01); *A61Q 17/04* (2013.01)

(58) Field of Classification Search
CPC ........ A61K 8/92; A61K 8/891; A61K 8/0245; A61K 8/025; A61K 8/731; A61K 2800/413; A61Q 1/10; A61Q 1/12; A61Q 1/02; A61Q 1/08; A61Q 17/04
See application file for complete search history.

(56) References Cited

U.S. PATENT DOCUMENTS

| | | | |
|---|---|---|---|
| 5,747,007 A | 5/1998 | Song et al. | |
| 2004/0156811 A1* | 8/2004 | Lynch | A61Q 1/12 424/70.13 |
| 2010/0055140 A1* | 3/2010 | Ogami | A61Q 1/12 424/401 |
| 2014/0037816 A1 | 2/2014 | Bakeev et al. | |
| 2014/0335136 A1 | 11/2014 | Brieva et al. | |
| 2015/0152197 A1 | 6/2015 | Akhlaghi et al. | |
| 2017/0260298 A1* | 9/2017 | Andrews | A61K 8/0241 |

FOREIGN PATENT DOCUMENTS

| | | | |
|---|---|---|---|
| CN | 104 644 472 A | | 5/2015 |
| CN | 106 109 329 A | | 11/2016 |
| WO | WO 8800039 A | * | 1/1988 |
| WO | 2013/033833 A1 | | 3/2013 |
| WO | 2016/015148 A1 | | 2/2016 |
| WO | WO 2016/015148 A1 | * | 2/2016 |

OTHER PUBLICATIONS

International Search Report and Written Opinion of the International Searching Authority dated Feb. 13, 2018 in corresponding International application No. PCT/EP2017/080981; 9 pages.
International Search Report and Written Opinion of the International Searching Authority dated Feb. 12, 2018 in corresponding International Application No. PCT/EP2017/080989; 12 pages.
McGill University, https://escholarship.mcgill.ca/concem/theses/kk91fp669?locale=en accessed Oct. 5, 2020, originally published 2015, 3 pages printed.
Higuchi et al., "Minimum rotation speed to prevent coning phenomena in compendium paddle dissolution apparatus." European Journal of Pharmaceutical Sciences, vol. 65, 2014, pp. 74-78.

* cited by examiner

*Primary Examiner* — Blessing M Fubara
(74) *Attorney, Agent, or Firm* — Maier & Maier, PLLC

(57) ABSTRACT

A powdery cosmetic composition in the form of a compacted powder including, in a physiologically acceptable medium, (i) a pulverulent phase including nanocrystalline cellulose, and (ii) a binder phase. Also, the use of the pulverulent phase for the preparation of a cosmetic composition in the form of compacted powder with satisfactory cohesive properties.

27 Claims, No Drawings

POWDERY COSMETIC COMPOSITION COMPRISING NANOCRYSTALLINE CELLULOSE

TECHNICAL FIELD

The present invention relates to a powdery cosmetic composition in the form of a compacted powder.

BACKGROUND OF THE INVENTION

Compacted powders are used in the field of makeup cosmetic compositions mainly to color and to mattify the skin, but also to mask skin imperfections such as pores, marks or wrinkles.

This galenical form is particularly appreciated by users for their non-greasy feel and their softness.

These compositions combine a high content of pulverulent phase, for example at least 30% relative to the total weight of the composition, with a fatty phase conventionally known as "binder phase". The pulverulent phase comprises fillers, from different shapes and chemical natures. It may also comprise at least one coloring agent such as pigments and/or nacres. The binder phase may be liquid and/or solid, and its main functions are to ensure sufficient cohesion to the final composition, i.e. to prevent its fragmentation caused by impacts, to allow a good take of the product by the consumer, and to facilitate the adhesion to the skin of the pulverulent phase.

To obtain a cosmetic composition in the form of a compacted powder, it is known from the prior art to mix the pulverulent phase and the binder phase. Then, a compaction step, usually by mechanical pressure, is necessary to provide sufficient cohesion to the final product.

However, depending on the type of powders used, the ease of compacting is variable. Indeed, certain fillers lack the ability to be compacted. These include but are not limited to pigments, nacres and certain fillers. Consequently, their presence in a cosmetic composition intended to be formulated in the form of a compacted powder may significantly affect the cohesion of the resulting compacted powder. Besides, the powdery composition may become difficult to compact, and a higher pressure is needed to obtain a compacted powder.

In addition, compacted powders may have the drawback of being be fragile, or may brittle or may have poor impact strength, i.e. breaks more easily when the product is dropped.

One solution known from the prior art to improve the cohesion and impact resistance of compacted powders consist in increasing the amount of binder phase. However, increasing the amount of liquid binder may lead to a waxy composition, i.e. which hardens during use to the point that it cannot be taken up anymore, which is clearly desirable to avoid. On the other side, solid binders have the drawback of having a bad touch; therefore, an excess amount of solid binder in a composition in the form of a compacted powder may affect the sensoriality of the final product, and may also affect the ability of the product to be easily taken up.

Another solution known from the prior art to improve the cohesion and impact resistance of compacted powders consist in increasing the compression force when compacting the powder. This may lead to a harder compacted powder, but it may become impossible to be sampled and the product may lose its organoleptic benefits such as softness or creamy. Besides, it is complicated or even impossible to perform high pressure at an industrial level, due to technical requirements.

Thereby, there remains a need for having powdery cosmetic compositions being easily compacted into a compacted powder showing good cohesion, while meeting the expectations of consumers in both sensory and makeup results.

Furthermore, when incompactable fillers are present in large quantities, we lack a satisfactory technical solution that can easily be implemented industrially.

SUMMARY OF THE INVENTION

The present inventors have discovered that the incorporation of nanocrystalline cellulose particles in the pulverulent phase of a powdery composition allows to overcome the abovementioned drawbacks of the prior art. The inclusion of nanocrystalline cellulose in powdery compositions confers enhanced compaction properties and enhanced texture. Furthermore, it confers excellent homogeneity and cohesion to the final product, while providing excellent usability and enhanced cosmetic properties.

The present invention is therefore directed to a cosmetic composition in the form of a compacted powder comprising a pulverulent phase and a binder phase, characterized in that the pulverulent phase comprises nanocrystalline cellulose.

According to one embodiment, the compositions according to the present invention are easy to compact, i.e. do not require a high compression force, even when they contain a large amount of incompactable compounds such as pigments and/or nacres.

According to another embodiment, the presence of nanocrystalline cellulose in the powdery compositions according to the invention allows to reduce the compaction pressure during the manufacturing process, and therefore, fulfilling the industrial requirements, without deteriorating the cohesion of the product.

According to another embodiment, the compositions in the form of compacted powders according to the invention thus obtained exhibits outstanding cohesion and high impact strength when dropped.

According to another embodiment, the compositions according to the present invention exhibit satisfactory disintegration of the product by the user. Due to its smooth surface, nanocrystalline cellulose particles provide a smooth skin feel to consumers when using the compositions according to the present invention, as well as a natural makeup result.

According to another embodiment, the compositions in the form of compacted powders according to the invention exhibit excellent concealing of surface imperfections, especially pore concealing.

Therefore, one aim of the present invention is to provide good compactability to a powdery cosmetic composition, even when it comprises a large amount of pigments and/or nacres.

Another aim of the present invention is to obtain a compacted powder which is resistant to impact.

Another aim of the present invention is to obtain a compacted powder with good taking overtime, and thus does not become waxy upon use.

Another aim of the present invention is to obtain a compacted powder with good cosmetic properties. It exhibits a good makeup result, good wear properties, a good adhesion to the skin, and that is comfortable.

Another aim of the present invention is to obtain a compacted powder with good organoleptic properties and good sensory properties, e.g. comfort, lightness and softness to the touch.

Thus, the compositions according to the invention especially find an advantageous application in the field of products for making up the skin in the form of compacted powders, such as face powders, foundations, blushers, highlighters, eyeshadows, eyebrow products, concealers or makeup products for the body.

The present invention relates to compositions in the form of compacted powders comprising, in a physiologically acceptable medium, a pulverulent phase comprising nanocrystalline cellulose, and a binder phase.

Another object of the invention is to provide a cosmetic composition in the form of a compacted powder comprising a pulverulent phase comprising nanocrystalline cellulose, and a binder phase, wherein said nanocrystalline cellulose is a functionalized nanocrystalline cellulose.

Another object of the invention is to provide a cosmetic composition in the form of a compacted powder comprising a pulverulent phase comprising nanocrystalline cellulose, and a binder phase, wherein said functionalized nanocrystalline cellulose is carboxylated nanocrystalline cellulose.

Another object of the invention is to provide a cosmetic composition in the form of a compacted powder comprising a pulverulent phase comprising nanocrystalline cellulose, and a binder phase, wherein said carboxylated nanocrystalline cellulose is in the form of a nanocrystalline cellulose carboxylate salt.

Another object of the invention is to provide a cosmetic composition in the form of a compacted powder comprising a pulverulent phase comprising nanocrystalline cellulose, and a binder phase, wherein said nanocrystalline cellulose carboxylate salt is a nanocrystalline cellulose sodium carboxylate.

Another object of the invention is to provide a cosmetic composition in the form of a compacted powder comprising a pulverulent phase comprising nanocrystalline cellulose, and a binder phase, wherein said nanocrystalline cellulose sodium carboxylate is produced by the method comprising the steps of:
a) providing cellulose,
b) mixing said cellulose with a peroxide, thereby producing a reaction mixture,
c) heating the reaction mixture, and/or exposing the reaction mixture to UV radiation, and
d) salifying the reaction mixture.

Another object of the invention is to provide a cosmetic composition in the form of a compacted powder comprising a pulverulent phase comprising nanocrystalline cellulose, and a binder phase, wherein said nanocrystalline cellulose has a spherical or ovoid shape.

Another object of the invention is to provide a cosmetic composition in the form of a compacted powder comprising a pulverulent phase comprising nanocrystalline cellulose, and a binder phase, wherein said nanocrystalline cellulose has an average particle size of less than about 20 μm, preferably from 2 μm to 10 μm. The average particle size is the particle size distribution D50, also known as the median diameter or the medium value of the particle size distribution, it is the value of the particle diameter at 50% in the cumulative distribution. The particle size distribution is determined by Scanning Electron Microscopy (SEM).

Another object of the invention is to provide a cosmetic composition in the form of a compacted powder comprising a pulverulent phase comprising nanocrystalline cellulose, and a binder phase, wherein said nanocrystalline cellulose is present in an amount of from about 0.1% to about 90% by weight relative to the total weight of the composition, preferably from 1% to 50%, more preferably from 3% to 30%.

Another object of the invention is to provide a cosmetic composition in the form of a compacted powder comprising a pulverulent phase comprising nanocrystalline cellulose, and a binder phase, wherein said pulverulent phase is present in an amount of greater than or equal to 30% by weight relative to the total weight of the composition, preferably at least 40%, and more preferably from 50% to 90%.

Another object of the invention is to provide a cosmetic composition in the form of a compacted powder comprising a pulverulent phase comprising nanocrystalline cellulose, and a binder phase, wherein said pulverulent phase comprises fillers which may be chosen from the group consisting of organic fillers and inorganic fillers.

Another object of the invention is to provide a cosmetic composition in the form of a compacted powder comprising a pulverulent phase comprising nanocrystalline cellulose and fillers, and a binder phase, wherein said pulverulent phase contains at least one coloring agent which may be chosen from pigments and/or nacres. According to one embodiment, the at least one coloring agent represents at least 0.1% by weight relative to the total weight of the composition, preferably from 0.1% to 60%.

Another object of the invention is to provide a cosmetic composition in the form of a compacted powder comprising a pulverulent phase comprising nanocrystalline cellulose, and a binder phase, wherein said binder phase is present in an amount of at least 10% by weight relative to the total weight of the composition.

Another object of the invention is to provide a cosmetic composition in the form of a compacted powder comprising a pulverulent phase comprising nanocrystalline cellulose, and a binder phase, wherein said binder phase comprises a liquid binder phase and a solid binder phase. According to one embodiment, said liquid binder phase may comprise at least one non-volatile oil, which may be selected from the group consisting of non-volatile hydrocarbon-based oils and non-volatile silicone-based oils.

Another object of the invention is to provide a cosmetic composition in the form of a compacted powder comprising a pulverulent phase comprising nanocrystalline cellulose, and a binder phase, wherein the solid binder phase comprises at least one component selected from the group consisting of waxes and metallic soaps.

Another object of the invention is to provide a cosmetic composition in the form of a compacted powder comprising a pulverulent phase comprising nanocrystalline cellulose, and a binder phase, wherein the compacted powder further comprises UV screening agents which may be chosen from mineral UV screening agents and organic UV screening agents.

Another object of the invention is to provide a cosmetic composition in the form of a compacted powder comprising a pulverulent phase comprising nanocrystalline cellulose, and a binder phase, wherein the composition further comprises at least one additional ingredient chosen from preservatives, cosmetic active ingredients, moisturizers, surfactants and/or fragrances.

Other characteristics, aspects and advantages of the present invention will become apparent on reading the detailed description which follows.

DETAILED DESCRIPTION

The term "pulverulent phase" as used herein include any compound or mixture of compounds in solid form at room temperature, and whose melting point is higher than 200° C.

The pulverulent phase represents at least 30% relative to the total weight of the compositions according to the present invention, preferably from 35% to 99% by weight, more preferably from 40% to 95% by weight, and better still from 50% to 90% by weight.

The components of the pulverulent phase may be surface-coated or not surface-coated. Among the surface-coatings that may be used in the present invention, mention may be made of aluminium hydroxide; alumina; polyurethane derivatives; polyquarternium derivatives; silicone derivatives such as triethoxycaprilylsilane (OTS coating from Daito Kasei), triethoxysilylethyl polydimethylsiloxyethylhexyl dimethicone, acrylates/dimethicone copolymer (FSA coating from Daito Kasei), methicone or dimethicone; amino-acid derivatives or N-acylamino acids or salts thereof such as sodium lauroyl glutamate, sodium lauroyl aspartate, lysine, disodium stearoyl glutamate, lauroyl lysine; fluoro derivatives such as perfluoroalkylsilanes, perfluoroalkylsilazanes, perfluoroalkyl phosphates, C9-C15 fluoroalcohol phosphates; lecithin derivatives such as hydrogenated lecithin; alkyl titanated derivatives such as isopropyl titanium triisostearate; silica; silicates such as potassium aluminium silicate; fatty acid derivative such as stearic acid; metallic soaps such as aluminium dimyristate, aluminium stearate, magnesium myristate, metal oxides such as titanium dioxide, zinc oxide or iron oxide; and mixture thereof.

According to the present invention the pulverulent phase comprises nanocrystalline cellulose, also referred to as "NCC". Nanocrystalline cellulose is derived from native cellulose from which the amorphous part is removed to keep only the crystalline part.

According to the present invention, the amorphous part of native cellulose is advantageously removed by oxidative hydrolysis of native cellulose using a peroxide, such as hydrogen peroxide, an organic peroxide or a mixture thereof. This process of dissolution of the amorphous part of native cellulose using a peroxide produces nano-crystallites of cellulose, which are then assembled into larger particles corresponding to said nanocrystalline cellulose or NCC.

According to a first embodiment of the present invention, said nanocrystalline cellulose is functionalized, i.e. it has undergone a surface modification to produce functionalized nanocrystalline cellulose. According to a preferred embodiment, said functionalized nanocrystalline cellulose is a carboxylated nanocrystalline cellulose.

Advantageously, carboxylated nanocrystalline cellulose may undergo total or partial salification to produce nanocrystalline cellulose carboxylate salt.

According to another embodiment, the nanocrystalline cellulose carboxylate salt according to the present invention is produced by the method comprising the steps of:
a) providing cellulose,
b) mixing said cellulose with a peroxide, thereby producing a reaction mixture,
c) heating the reaction mixture, and/or exposing the reaction mixture to UV radiation, and
d) salifying the reaction mixture.

According to another embodiment, the assemblage of nano-crystallites of cellulose into particles of nanocrystalline cellulose is achieved by spray-drying.

According to another embodiment, said particles of nanocrystalline cellulose have a spherical or ovoid shape, or a mixture thereof.

According to another embodiment, nanocrystalline cellulose has an average particle size of less than 20 μm, preferably less than 15 μm, more preferably between 2 μm and 10 μm.

According to another embodiment, nanocrystalline cellulose has an oil uptake of less than 60 mL/100 g, preferably between 45 and 55 mL/100 g, and more preferably between 48 and 52 mL/100 g. The oil uptake characterizes the ability to adsorb castor oil. It is determined by adding castor oil to 100 g of nanocrystalline cellulose powder. The oil uptake corresponds to the minimal amount of castor oil, in milliliters, required to obtain a firm and homogeneous paste.

According to another embodiment, nanocrystalline cellulose has a contact angle with water between 80° and 100°, preferably between 85° and 95°, and more preferably between 88° and 92°.

Preferentially nanocrystalline cellulose used in the present invention is nanocrystalline cellulose obtained by the process described in the disclosure of patent application WO 2016/015148, incorporated herein by reference.

Nanocrystalline cellulose may represent from about 0.1% to about 90% by weight relative to the total weight of the composition, preferably from 1% to 50%, more preferably from 3% to 30%.

The compositions according to the present invention may include at least one filler different from nanocrystalline cellulose. The term "filler" as used herein means a white or colorless solid particle, which is intended to give texture and body to cosmetic compositions. The fillers confer also softness, matity and uniformity to the cosmetic compositions.

A composition according to the present invention may advantageously have a content of fillers of at least 0.5% by weight relative to the total composition, preferably from 1% to 90% by weight, more preferably from 3% to 80% by weight, better still from 5% to 70%.

The fillers used in the compositions according to the present invention may be organic or inorganic.

The fillers used in the compositions according to the present invention may have a spherical, lamellar, ovoid, or globular shape or being in the form of fibers. They may also be in any intermediate shape between these defined shapes. The fillers used in the compositions according to the present invention may also be hollow particles, porous particles or non-porous particles. They may be surface-coated or not.

Among the inorganic fillers that may be used in the present invention, mention may be made of talc, boron nitride, mica, synthetic fluorphlogopite, hydroxyapatite, alumina, silk powder, pearl powder, barium sulfate powder, cellulose powder, microcrystalline cellulose powder, perlite, glass, ceramic; clays such as muscovite, phlogopite, kaolin, hectorite or bentonite; silica based-materials such as silica, fumed silica, or silica silylate; quartz, or gemstones such as gold or diamond powders.

The inorganic fillers that may also be used in the compositions according to the invention may also be chosen from silicates, such as magnesium aluminium silicate, aluminium silicate, calcium magnesium silicate, diatomaceous earth, or sodium magnesium silicate; and carbonates such as calcium carbonate or magnesium carbonate.

Among the organic fillers that may be used in the present invention, mention may be made of polyamide powders (Nylon® powders such as Nylon-6, Nylon-12, Nylon 6/12, or Polyamide-5), polytetrafluoroethylene polymer powders, polyurethane powders, polyethylene powders, acrylic polymer powders such as polymethyl methacrylate, methyl methacrylate, acrylates/ethylhexyl acrylate crosspolymer powders, copolymer of styrene and acrylic acid powders. The organic fillers that may also be used in the compositions according to the invention may also be chosen from silicone powders, such as silicone resin microbeads (Tospearl® from Toshiba), elastomeric organopolysiloxane powders, or elastomeric organopolysiloxane powders coated with silicone resin. Among these, mention may be made of polymethylsilsesquioxane, vinyl dimethicone/methicone silsesquioxane crosspolymer, trimethylsiloxysilicate, or diphenyl dimethicone/vinyl diphenyl dimethicone/silsesquioxane crosspolymer. The organic fillers may also be naturally-derived polymer powders, such as tapioca dextrin, or starch derivatives such as aluminium starch octenylsuccinate.

The fillers that may also be used in the compositions according to the invention may also be composite particles, for example composites of silica and titanium dioxide, composites of methyl methacrylate crosspolymer and polymethyl methacrylate.

As mentioned above, the pulverulent phase of the compositions according to the present invention may comprise at least one coloring agent chosen from pigments and nacres and mixture thereof. The term "coloring agent" is understood to mean a white or colored particle, which may be mineral or organic and from any particle size and shape, intended to impart a visual effect to the composition such as for example color effect by absorption or by optical interference.

The coloring agent may represent at least 0.1% relative to the total weight of the compositions according to the invention, preferably from 0.1% to 60%.

The pigments may be mineral or organic particles, they may be surface-coated or uncoated. They are intended to impart color or opacity to cosmetic compositions. Mineral pigments that may be used in the present invention include metal oxides and metal hydroxides such as titanium dioxide, iron oxide, zinc oxide, zirconium oxide, aluminium oxide, chromium oxide, manganese oxide, ultramarine blue, manganese violet, iron hydroxide, magnesium hydroxide, aluminium hydroxide, chromium hydroxide, and mixture thereof. Organic pigments that may be used in the present invention include dyes and lakes such as FD&C dyes or D&C dyes, cochineal carmine.

The term "nacre" is understood to mean white or colored particles of any form, whether or not iridescent, which impart a color effect via optical interference. They may be constituted by a substrate at the surface of which is preferably deposited at least one layer of at least one material. This material may advantageously be chosen from metal oxide, organic dyestuff or mixture thereof. The substrate may be of any material, and have any shape and any particle size. When the nacre has a multilayer structure, these layers may have the same thickness or have different thickness, and they may be of the same material or of different materials.

The substrate may be selected from mica, alumina, synthetic fluorphlogopite, sericite, glass, silica, silicates such as borosilicate, or aluminosilicate. The metal oxide may be chosen from titanium dioxide, iron oxide, tin oxide, silver oxide, bismuth oxychloride, and chromium oxide. The organic dyestuff may be chosen from lakes and dyes.

The compositions according to the present invention comprise at least a binder phase. The binder phase according to the invention advantageously represents at least 10% relative to the total weight of the compositions, preferably from 12% to 50%, more preferably from 15% to 30%

As mentioned above, the binder phase may include at least one liquid binder phase and/or at least one solid binder phase.

The term "liquid" refers to compounds in a liquid state at room temperature (i.e. 20° C.) and atmospheric pressure (i.e. $1.013 \times 10^5$ Pa).

The term "oil" refers to any compound that is not miscible in water and which is liquid at room temperature (i.e. 20° C.) and atmospheric pressure (i.e. $1.013 \times 10^5$ Pa).

The liquid binder phase advantageously includes at least one non-volatile oil, which may be hydrocarbon-based oil, silicone-based oil or a mixture thereof. The oils according to the invention may be synthetic or from natural origin.

The term "non-volatile oil" is understood to mean any liquid oil which is not capable of evaporating on contact with the skin, and thus remaining on the skin.

The term "hydrocarbon-based oils" means oils mainly containing carbon atoms and hydrogen atoms, and which may also comprise one or more functional group selected from alcohol, ether, ester, fluoro and/or carboxylic acid groups.

The term "silicone-based oils" means oils containing silicon atoms but also oxygen, carbon and hydrogen atoms. Silicone-based oils may also comprise one or more functional group such as alcohol, ether, ester, fluoro and/or carboxylic acid groups.

Silicone-based oils include but are not limited to linear and cyclic non-volatile polydimethylsiloxanes, polymethylphenylsiloxanes, phenyl dimethicones, phenyl trimethicones; polysiloxanes modified with fatty acids fatty alcohols, alkylene oxyalkylene groups or, amine group; fluorosilicones or perfluoro silicone oils;

Hydrocarbon-based oils include hydrocarbon oils, esters of fatty acids, fatty alcohols, fatty acids and/or vegetable oils.

Hydrocarbon oils which may be linear or branched, saturated or unsaturated, such as liquid paraffins, mineral oil, squalane, squalene, polydecenes, polybutenes and derivatives;

Esters of fatty acids of general formula $R_1COOR_2$ wherein $R_1$ represents a linear or branched fatty acid residue containing from 1 to 40 carbon atoms, preferably from 1 to 30 carbon atoms, more preferably from 1 to 22 carbon atoms, and $R_2$ represents a hydrocarbon-based chain which may be linear or branched too, and containing from 1 to 40 carbon atoms. These two carbon chains may be saturated or unsaturated. The esters may also contain a polyalkylene glycol branching such as polypropylene glycol or polyethylene glycol branching, for example PPG-2 myristyl ether propionate. The compositions according to the invention may also comprise polyesters, i.e. compounds comprising more than one ester functional group such as diesters or triesters. Mention may be made of triglycerides formed by esterification of glycerol such as caprylic/capric triglyceride; esters of polyglycerin such as polyglyceryl-2 triisostearate; triethylhexanoin, dicaprylyl carbonate or octyldodecyl stearoyl stearate. The acid residue may also be cyclic, such as in esters of benzoic acid or esters of salicylic acid.

Suitable fatty acid esters include without limitation isononyl isononanoate, isopropyl myristate, 2 ethylhexyl palmitate, hexyl laurate, diisostearyl malate, C12-15 Alkyl Ethylhexanoate, cetyl ethylhexanoate, octyl stearate, isodecyl neopentanoate, isostearyl palmitate, alkyl benzoates, butyl acetate, butyl lsostearale, butyl oleate, butyl octyl oleate, cetyl palmilale, ceyl oclanoale, celyl laurate, cetyl lactate, cetyl isononanoate, cetyl stearate, diisostearyl fumarate, diisostearyl malale, neopentyl glycol dioctanoate, dibutyl sebacate, di-$C_{12-13}$ alkyl malate, dicetearyl dimer dihnoleate, dicetyl adipate, dusocetyl adipate, dusononyl adipate, dusopropyl dunerate, triisostearyl trihnoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl lsononate, isohexyl neopentanoate, isohexadecyl stearate, isopropyl isostearate, n-propyl myristate, isopropyl mynstate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-C[12-13]-alkyl citrate, tricapryhn, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl) succinate, tocopheryl acetate, tripropylene glycol dineopentanoate, cetyl octanoate, cetyl isooctanoate, octyldodecyl myristate, isopropyl palmitate, cetyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, bis-behenyl/isostearyl/phytosteryl dimer dilinoleyl dimer dilinoleate, phytosteryl/behenyl/octyldodecyl/isostearyl lauroyl glutamate, caprylic/capric triglyceride, and triethylhexanoin.

Fatty alcohols, preferably having from 5 to 40 carbon atoms such as octyldodecanol and oleyl alcohol.

Fatty acids preferably having from 5 to 40 carbon atoms such as linoleic or linolenic acid.

Vegetable oils and derivatives, such as soybean oil, jojoba oil, olive oil, macadamia oil, liquid *Butyrospermum parkii* (shea butter), castor oil, camellia oil, gardenia oil, avocado oil, coconut oil, *Argania spinosa* kernel oil, corn oil, cottonseed oil, linseed oil, mink oil, soybean oil, grape seed oil, sesame oil, maize oil, rapeseed oil, sunflower oil, peanut oil, teas seed oil, rice bran oil.

Sarcosine derivatives such as isopropyl lauroyl sarcosinate.

According to one particular embodiment, the liquid binder phase comprises non-volatile hydrocarbon-based oils.

According to one embodiment, the compositions according to the invention may comprise at least one solid binder phase. The term "solid binder phase" used herein means a binder phase which is solid at room temperature (i.e. 20° C.) and atmospheric pressure (i.e. $1.013 \times 10^5$ Pa).

Advantageously, the solid binder phase is composed of one or more compounds chosen from metallic soaps, waxes, specific synthetic polymers and/or natural polymers in powder form, pasty compounds or mixture thereof. The solid binder phase in the form of particles may be coated with at least one surface coating listed above, or it may be not coated.

Metallic soaps may be chosen from the metal soaps of fatty acids having from 5 to 30 carbon atoms.

Non-limiting examples of metallic soaps that may be used include, magnesium stearate, magnesium myristate, zinc stearate or mixture thereof.

The waxes that are suitable for the present invention have a melting point is comprised in the range from 30° C. and 200° C. The compounds that may be used in the present invention include natural waxes such as those of animal origin, vegetable origin or mineral origin, and synthetic waxes.

Non-limiting example of waxes that may be used in the present invention include but are not limited to beeswax, lanolin wax and derivatives, jojoba wax, shellac wax, carnauba wax, candelilla wax, castor wax, bayberry wax, soy wax, hardened coconut oil, palm kernel oil, cacao butter, polycosanols, ozokerite wax, ceresin wax, paraffin waxes, microcrystalline waxes, vaseline, Fischer-Tropsch waxes, polyolefin waxes such as polyethylene wax, polyethylene glycol wax, hydrogenated polyisobutene, and mixture thereof. Mention may also be made of fatty acid esters or diesters solid at room temperature, such as Stearyl/PPG-3 Myristyl ether dimer dilinoleate or isostearyl hydroxystearate; silicone waxes such as C24-28 alkyl methicone or stearoxymethicone & dimethicone copolymer; micronized waxes, i.e. waxes in powder form, such as polypropylene micronized wax, carnauba wax microbeads.

Other suitable compounds that may be used as solid binder in the present invention include but are not limited to synthetic and natural polymers such as Polymethyl Methacrylate HDI/Trimethylol Hexyllactone Crosspolymer & silica powders, Polyethylene powders, corn starch powders and the like.

The compositions according to the invention may also comprise at least one UV screening agent chosen from mineral and/or organic sunscreen agents.

Examples of the inorganic sunscreens include pigments and nanopigments formed from coated or uncoated metal oxides. Among metal oxides, mention may be made of titanium oxide, iron oxide, zinc oxide, zirconium oxide and cerium oxide nanopigments, which are all well-known as UV photoprotective agents.

Examples of organic sunscreens include dibenzoylmethane derivatives such as butyl methoxydibenzoylmethane (for example, a product commercially available from HOFFMANN LA ROCHE under the trade name of Parsol 1789); cinnamic acid derivatives such as octyl methoxycinnamate (for example, a product commercially available from HOFFMANN LA ROCHE under the trade name of Parsol MCX); salicylates; para-aminobenzoic acids; β,β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; and anthranilic acid derivatives, all of which may be coated or encapsulated.

The compositions according to the present invention may also comprise additional ingredients usually used in cosmetics, such as preserving agents, cosmetic active ingredients, moisturizers, and/or fragrances.

The preserving agents that may be used include for example Ammonium silver zinc aluminium silicate, chlorophenesin, potassium sorbate, sodium dehydroacetate, and mixture thereof.

Among the cosmetic active ingredients that may be used in the present invention, mention may be made of whitening agents, brightening agents, antioxidant agents, anti-wrinkles agents, antiseborrheic agents, plant extracts, and mixture thereof.

Non-limiting examples of active ingredients include vitamin derivatives, such as tocopheryl actetate, ascorbic acid derivatives such as ascorbyl glucoside, Niacinamide, Licorice extract, *Kalanchoe pinnata* leaf extract, *Vanilla planifolia zextract*.

The compositions according to the present invention may aslo include at least one surfactant. Non-limiting example include sorbitan esters such as sorbitan sesquiisostearate, and silicone-based surfactant such as lauryl PEG-9 polydimethyl siloxyethyl dimethicone.

Drop Tests

The examples which follow are used to illustrate the invention without however presenting a restrictive character. In these examples, the quantities of the ingredients compositions are given in weight percentage compared to the total weight of the composition.

In order to demonstrate the influence of nanocrystalline cellulose, the applicant has formulated series of seven sample of four compacted powders with varying pulverulent phases, and then the cohesion was evaluated by the drop test.

To do so, 10.5 g of each composition was put in a crucible, and compacted with a pressure of 30 bar. The compositions are reported in table 1, where each ingredient is represented by the weight percentage relative to the total weight of the composition.

TABLE 1

Compacted powders composition in weight percent

| Ingredients list (COMMERCIAL NAME) | Compositions | | | |
|---|---|---|---|---|
| | 1 | 2 | 3 | 4 |
| POLYMETHYL METHACRYLATE & HDI/TRIMETHYLOL HEXYLLACTONE CROSSPOLYMER & SILICA (EPU-2X) | 6.00 | 6.00 | 6.00 | 6.00 |
| SYNTHETIC FLUORPHLOGOPITE & TRIETHOXYCAPRYLYL SILANE & ALUMINUM HYDROXIDE (CS-PDM-10L) | 6.00 | 6.00 | 6.00 | 6.00 |
| TITANIUM DIOXIDE & STEARIC ACID & ALUMINA & SILICA (UV-TITAN M160) | 15.00 | 15.00 | 15.00 | 15.00 |
| ZINC OXIDE & TRIETHOXYCAPRYLYLSILANE (OTS-5 MZ-500) | 5.00 | 5.00 | 5.00 | 5.00 |
| ACRYLATES/ETHYLHEXYL ACRYLATE CROSSPOLYMER (MAKIBEADS SP10) | 4.00 | 4.00 | 4.00 | 4.00 |
| VINYL DIMETHICONE/METHICONE SILSESQUIOXANE CROSSPOLYMER (KSP-100) | 5.00 | 5.00 | 5.00 | 5.00 |
| MAGNESIUM CARBONATE (BASIC MAGNESIUM CARBONATE) | 4.00 | 4.00 | 4.00 | 4.00 |
| CHLORPHENESIN (ELESTAB CPN ULTRAPUR) | 0.03 | 0.03 | 0.03 | 0.03 |
| SODIUM DEHYDROACETATE (GEOGARD 111S) | 0.08 | 0.08 | 0.08 | 0.08 |
| SILICA (SUNSPHERE H53) | 1.00 | 1.00 | 1.00 | 1.00 |
| AMMONIUM SILVER ZINC ALUMINUM SILICATE (ZEOMIC AW 10N) | 0.60 | 0.60 | 0.60 | 0.60 |
| POLYACRYLIC ACID & ZINC GLUCONATE (SEPITRAP 101C) | 0.30 | 0.30 | 0.30 | 0.30 |
| 70% of surface-treated pigments grinded in 30% of aluminium dimyristate-treated talc | 10.00 | 10.00 | 10.00 | 10.00 |
| Preservatives | 4.81 | 4.81 | 4.81 | 4.81 |
| DIMETHICONE (KF-96A-10CS) | 3.00 | 3.00 | 3.00 | 3.00 |
| TRIETHYLHEXANOIN (TIO) | 3.00 | 3.00 | 3.00 | 3.00 |
| LAURYL PEG-9 POLYDIMETHYLSILOXYETHYL DIMETHICONE (KF-6038) | 1.50 | 1.50 | 1.50 | 1.50 |
| TOCOPHERYL ACETATE (DL-ALPHA-TOCOPHERYL ACETATE) | 0.05 | 0.05 | 0.05 | 0.05 |
| ETHYLHEXYL METHOXYCINNAMATE & BHT (PARSOL MCX) | 5.00 | 5.00 | 5.00 | 5.00 |
| NANOCRYSTALLINE CELLULOSE | 25.63 | — | — | — |
| CELLULOSE (CELLULOBEADS D-5) | — | 25.63 | — | — |
| MICA & TITANIUM DIOXIDE (CI 77891) (TIMIRON SUPER SILVER FINE 117219) | — | — | — | — |
| MICROCRYSTALLINE CELLULOSE (AVICEL PC 105) | — | — | 25.63 | — |
| POLYETHYLENE (ASENSA CL 110) | — | — | — | 25.63 |
| TOTAL (%) | 100 | 100 | 100 | 100 |

Each compacted powder samples was subjected to standardized drops over a height of 30 cm onto a metallic plate with the base of the crucible oriented towards the receiving surface of the metallic plate. The operation was repeated for all samples of each powder until it breaks.

The average numbers of drops before breaking were calculated on the seven samples for each powder compositions and are reported in table 2.

TABLE 2 average number of drops before breaking

| Composition no | Average number of drops before breaking |
|---|---|
| 1 | 7.83 ± 0.9 |
| 2 | 5.3 ± 1.24 |
| 3 | 4 ± 0.58 |
| 4 | 6 ± 0.82 |

The number of drops before breaking is representative of the cohesion of the compacted powder.

Surprisingly, the inventors have found that the formulas comprising nanocrystalline cellulose require the greatest number of drops before breaking, in comparison with the other powders tested. Therefore, the incorporation of nanocrystalline cellulose allows improving the cohesion properties of compacted powders.

The invention claimed is:

1. A powdery cosmetic composition in the form of a compacted powder comprising, in a physiologically acceptable medium,
   (i) a pulverulent phase comprising functionalized nanocrystalline cellulose, wherein said functionalized nanocrystalline cellulose is carboxylated nanocrystalline cellulose, and
   (ii) a binder phase.

2. The powdery cosmetic composition according to claim 1, wherein said carboxylated nanocrystalline cellulose is in the form of a nanocrystalline cellulose carboxylate salt.

3. The powdery cosmetic composition according to claim 2, wherein said nanocrystalline cellulose carboxylate salt is a nanocrystalline cellulose sodium carboxylate.

4. The powdery cosmetic composition according to claim 3, wherein said so nanocrystalline cellulose sodium carboxylate is produced by the method comprising the steps of:
   (a) providing cellulose,
   (b) mixing said cellulose with a peroxide, thereby producing a reaction mixture,
   (c) heating the reaction mixture, and/or exposing the reaction mixture to UV radiation, and
   (d) salifying the reaction mixture.

5. The powdery cosmetic composition according to claim 1, wherein said nanocrystalline cellulose has a spherical or ovoid shape.

6. The powdery cosmetic composition according to claim 1, wherein said nanocrystalline cellulose has an average particle size of less than about 20 μm.

7. The powdery cosmetic composition according to claim 1, wherein said nanocrystalline cellulose has an average particle size from about 2 μm to about 10 μm.

8. The powdery cosmetic composition according to claim 1, wherein said nanocrystalline cellulose is present in an amount of from about 0.1% to about 90% by weight relative to the total weight of the composition.

9. The powdery cosmetic composition according to claim 1, wherein said pulverulent phase is present in an amount of greater than or equal to 30% by weight relative to the total weight of the composition.

10. The powdery cosmetic composition according to claim 1, wherein said pulverulent phase comprises a filler.

11. The powdery cosmetic composition according to claim 10, wherein said filler is selected from the group consisting of organic fillers and inorganic fillers.

12. The powdery cosmetic composition according to claim 1, wherein said pulverulent phase contains at least one coloring agent.

13. The powdery cosmetic composition according to claim 12, wherein said least one coloring agent is selected from pigments and nacres.

14. The powdery cosmetic composition according to claim 12, wherein said at least one coloring agent is present in an amount of at least 0.1% by weight relative to the total weight of the composition.

15. The powdery cosmetic composition according to claim 14, wherein at least one coloring agent is present in an amount of from 0.1% to 60% by weight relative to the total weight of the composition.

16. The powdery cosmetic composition according to claim 1, wherein said binder phase is present in an amount of at least 10% by weight relative to the total weight of the composition.

17. The powdery cosmetic composition according to claim 1, wherein said binder phase comprises a liquid binder phase and/or a solid binder phase.

18. The powdery cosmetic composition according to claim 17, wherein said liquid binder phase comprises at least one non-volatile oil.

19. The powdery cosmetic composition according to claim 18, wherein said at least one non-volatile oil is selected from the group consisting of non-volatile hydrocarbon-based oils and non-volatile silicone-based oils.

20. The powdery cosmetic composition according to claim 17, wherein the solid binder phase comprises at least one component selected from the group consisting of waxes, metallic soaps and polymers in powder form.

21. The powdery cosmetic composition according to claim 1, wherein the compacted powder further comprises a UV screening agent.

22. The powdery cosmetic composition according to claim 21, wherein said UV screening agent is selected from the group consisting of mineral UV screening agents and organic UV screening agents.

23. The powdery cosmetic composition according to claim 1, wherein the compacted powder further comprises a preservative, a cosmetic active ingredient, a moisturizer, a surfactant or a fragrance.

24. The powdery cosmetic composition according to claim 1, wherein the powdery composition is selected from the group consisting of a face powder, a foundation, a blusher, a concealer, and an eyeshadow.

25. A method of preparing a cosmetic composition in the form of compacted powder with satisfactory cohesive properties comprising adding a pulverulent phase according to claim 1 to a cosmetic composition.

26. The powdery cosmetic composition according to claim 1, wherein said nanocrystalline cellulose is present in an amount from 1% to 50% by weight relative to the total weight of the composition.

27. The powdery cosmetic composition according to claim 1, wherein said pulverulent phase is present in an amount of at least 40%, by weight relative to the total weight of the composition.

* * * * *